US011737822B2

(12) United States Patent
Wang et al.

(10) Patent No.: US 11,737,822 B2
(45) Date of Patent: Aug. 29, 2023

(54) DISPERSIVE RETURN PAD WITH PHASE CHANGE MATERIAL FOR ACTIVE THERMAL MANAGEMENT DURING AN ABLATION PROCEDURE

(71) Applicant: Avent, Inc., Alpharetta, GA (US)

(72) Inventors: Ruoya Wang, Decatur, GA (US); Jennifer J. Barrett, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 825 days.

(21) Appl. No.: 16/043,696

(22) Filed: Jul. 24, 2018

(65) Prior Publication Data

US 2020/0030030 A1    Jan. 30, 2020

(51) Int. Cl.
*A61B 18/16* (2006.01)
*A61B 18/14* (2006.01)
*A61B 18/00* (2006.01)

(52) U.S. Cl.
CPC .......... *A61B 18/16* (2013.01); *A61B 18/1482* (2013.01); *A61B 2018/00083* (2013.01); *A61B 2018/00577* (2013.01); *A61B 2018/00714* (2013.01); *A61B 2018/167* (2013.01)

(58) Field of Classification Search
CPC .............. A61B 18/16; A61B 2018/167; A61B 18/1482
See application file for complete search history.

(56) References Cited

U.S. PATENT DOCUMENTS

| | | | |
|---|---|---|---|
| 3,848,600 A | * | 11/1974 | Patrick, Jr. ............. A61B 18/16 607/153 |
| 6,287,305 B1 | | 9/2001 | Heim et al. |
| 6,471,695 B1 | | 10/2002 | Behl |
| 6,533,781 B2 | | 3/2003 | Heim et al. |
| 7,377,919 B2 | | 5/2008 | Heim et al. |
| 8,021,360 B2 | | 9/2011 | Dunning et al. |
| 8,075,555 B2 | | 12/2011 | Truckai et al. |
| 8,562,603 B2 | | 10/2013 | Heim et al. |

(Continued)

FOREIGN PATENT DOCUMENTS

WO    WO 2007131248    * 11/2007    .......... A61N 1/0492
WO    WO 2012/116957 A1    9/2012

OTHER PUBLICATIONS

International Search Report and Written Opinion for PCT/US2019/043147, dated Oct. 29, 2019, 14 pages.

*Primary Examiner* — Linda C Dvorak
*Assistant Examiner* — Ryan T Clark
(74) *Attorney, Agent, or Firm* — Meunier Carlin & Curfman LLC

(57) ABSTRACT

A dispersive return pad for a radiofrequency ablation procedure includes a skin material adapted to be worn on a patient's skin, a conductive material positioned adjacent to the skin material, a non-conductive material surrounding the conductive material, and a phase-change material surrounding at least a portion of a side edge of the conductive material. Further, the phase-change material is configured to undergo a phase transition at a target temperature range corresponding to a non-damaging hyperthermic temperature range for the patient's skin. As such, the phase-change material is configured to absorb excess heating from the RF ablation procedure and to prevent burns to the patient's skin.

16 Claims, 5 Drawing Sheets

(56) References Cited

U.S. PATENT DOCUMENTS

| | | |
|---|---|---|
| 9,044,261 B2 | 6/2015 | Houser |
| 9,314,368 B2 | 4/2016 | Allison et al. |
| 9,439,712 B2 | 9/2016 | Sharonov |
| 9,526,566 B1 | 12/2016 | Johnson |
| 9,532,899 B2 | 1/2017 | Fahey et al. |
| 9,717,552 B2 | 8/2017 | Cosman et al. |
| 2008/0195089 A1 | 8/2008 | Thiagalingam et al. |
| 2008/0281310 A1* | 11/2008 | Dunning .............. A61N 1/0408 606/32 |
| 2009/0112202 A1* | 4/2009 | Young .................... A61B 18/16 606/33 |
| 2011/0166568 A1 | 7/2011 | Hagg et al. |
| 2016/0338759 A1 | 11/2016 | Schnitzler et al. |
| 2017/0015881 A1* | 1/2017 | Tanaka ..................... C09J 11/04 |

* cited by examiner

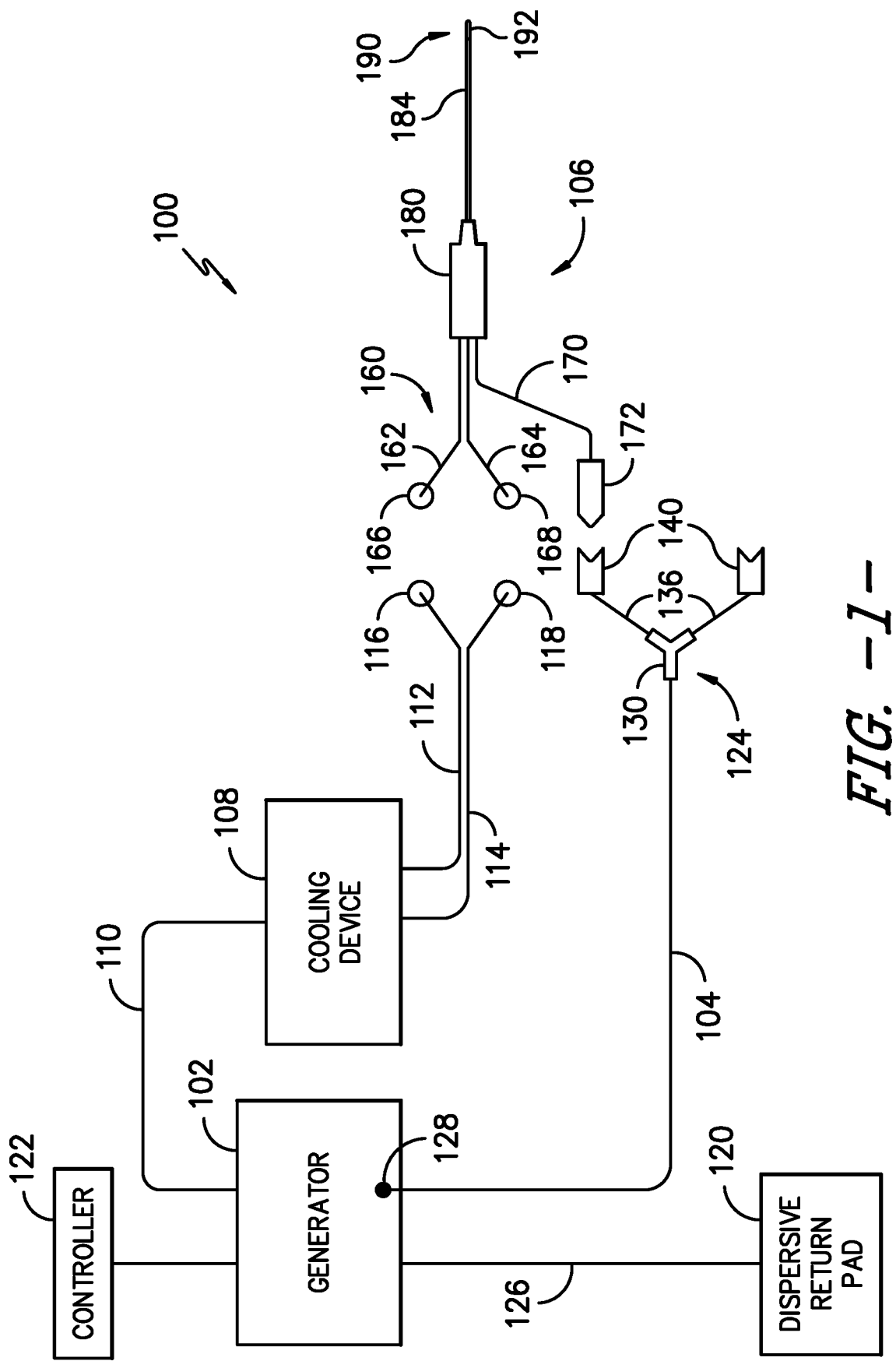
FIG. -1-

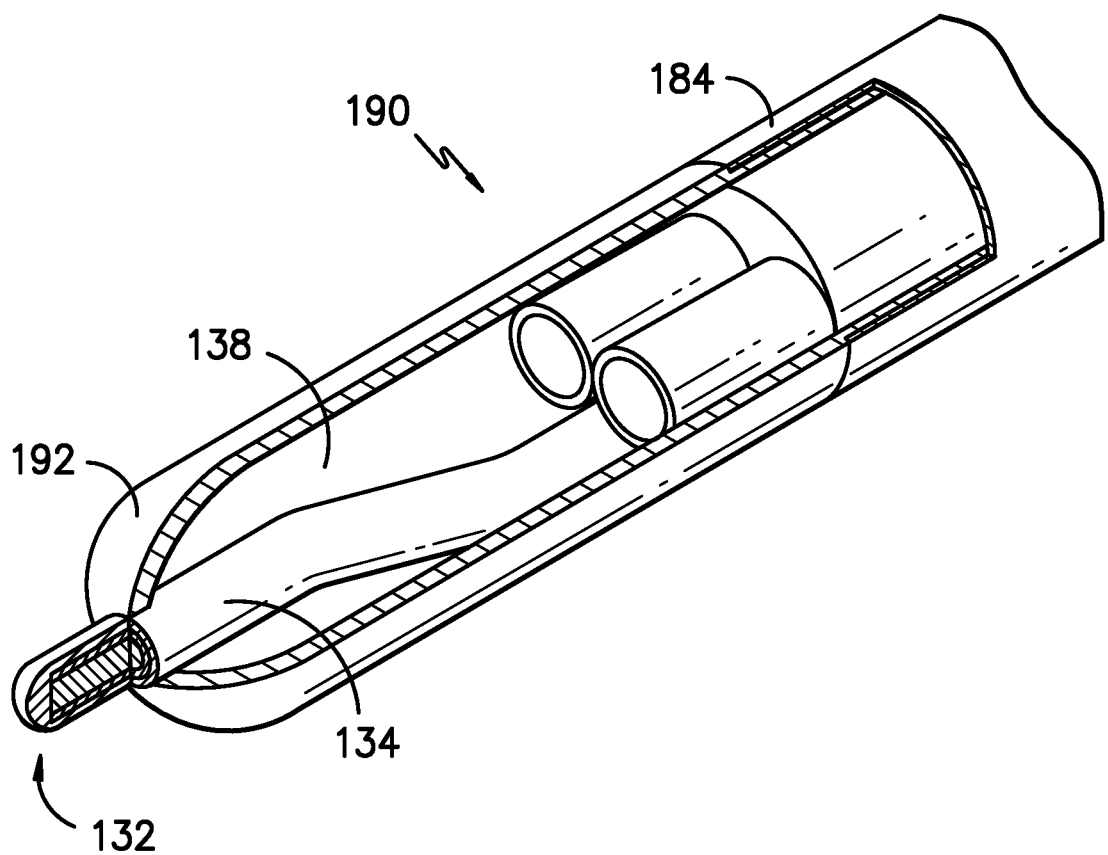
FIG. -2-

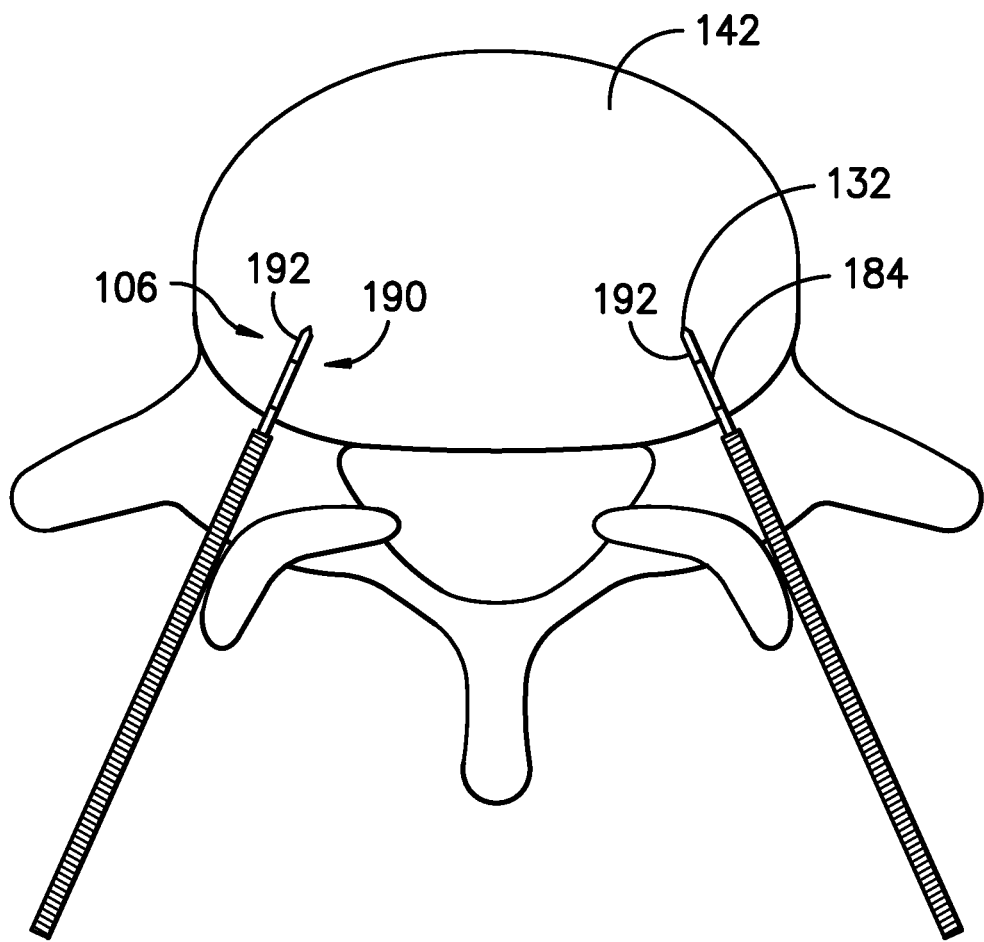
FIG. -3-

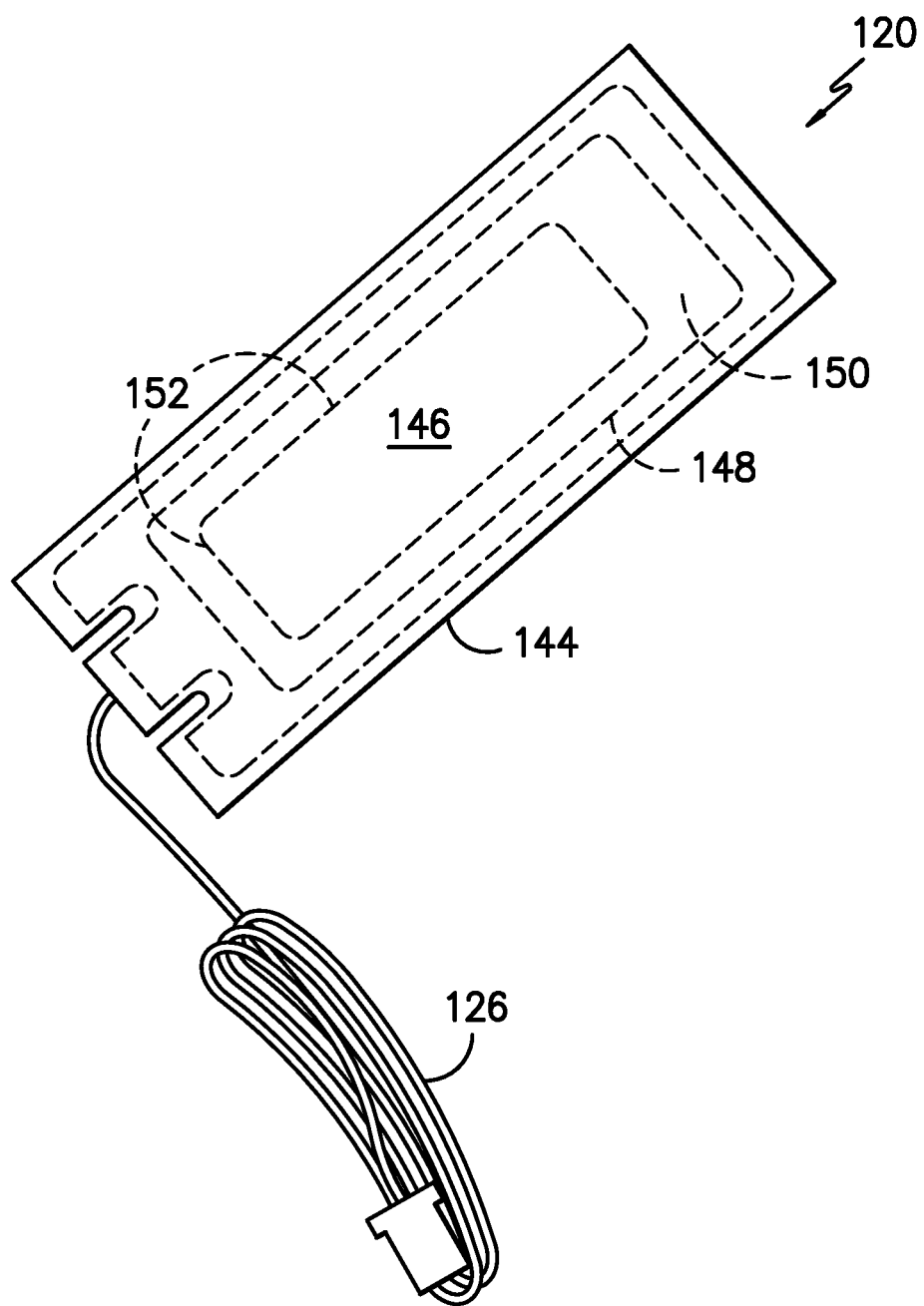
FIG. -4-

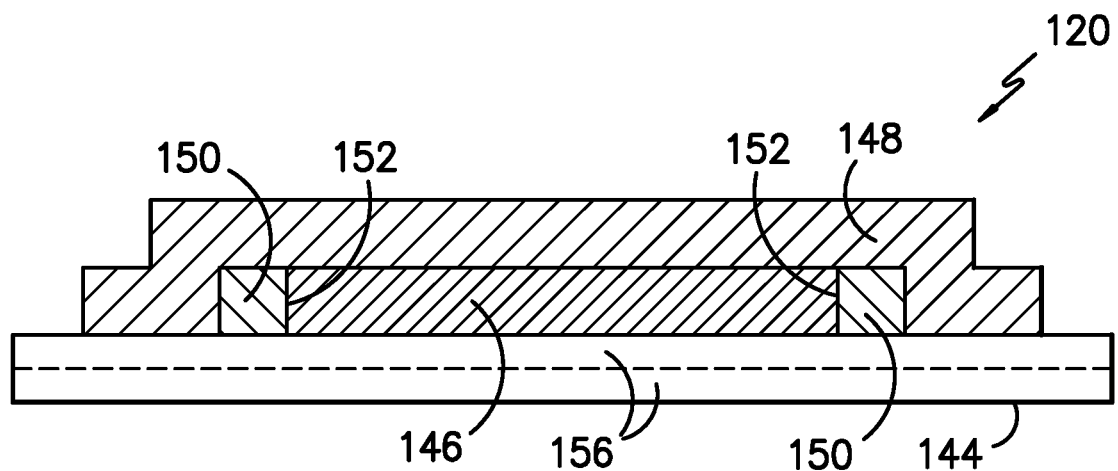
FIG. -5-
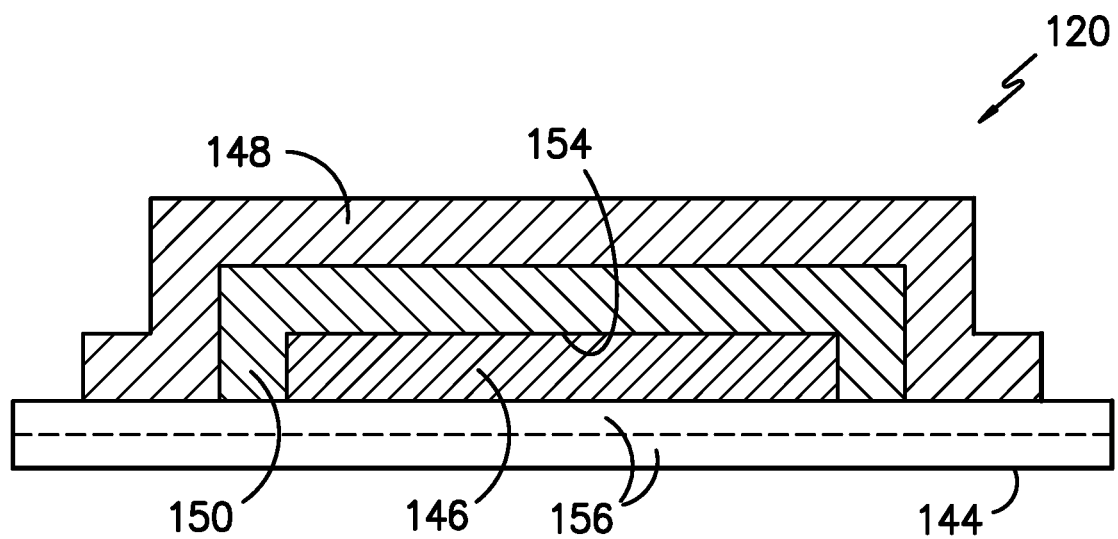
FIG. -6-

DISPERSIVE RETURN PAD WITH PHASE CHANGE MATERIAL FOR ACTIVE THERMAL MANAGEMENT DURING AN ABLATION PROCEDURE

FIELD OF THE INVENTION

The present invention relates generally to radiofrequency (RF) ablation, and more particularly to a system and method for active thermal management during an ablation procedure that utilizes a dispersive return pad with a phase change material.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues in respect to patient treatment for back pain. In joints, osteoarthritis is the most common form of arthritis pain and occurs when the protective cartilage on the ends of bones wears down over time.

The treatment of pain using high-frequency electrical current has been applied successfully to various regions of patients' bodies suspected of contributing to chronic pain sensations. For example, with respect to back pain, which affects millions of individuals every year, high-frequency electrical treatment has been applied to several tissues, including intervertebral discs, facet joints, sacroiliac joints as well as the vertebrae themselves (in a process known as intraosseous denervation). In addition to creating lesions in neural structures, application of radiofrequency energy has also been used to treat tumors throughout the body. Further, with respect to knee pain, which also affects millions of individuals every year, high-frequency electrical treatment has been applied to several tissues, including, for example, the ligaments, muscles, tendons, and menisci.

Radiofrequency ablation (RFA) is a minimally invasive therapy for treating chronic pain, cardiac arrhythmias, and tumors in many patients. RFA systems share similar components including the RF generator, active electrode/s, and a dispersive return pad (DRP). The DRP is adhered to the patient's skin and is designed to return the electrical energy from the patient's body back to the RF generator with negligible heating. Non-optimal skin interface conditions, improper placement or usage, and poor design can result in serious burns to the patient's skin.

With the increasing power of RFA generators, it has become critical to ensure sufficient dispersion of the current and mitigation of any DRP heating. Increasing the DRP's surface area is not always practical due to limitations in placement on the patient, system complexity, and/or cost.

The DRP is a disposable component that is designed to disperse and return the electrical current from the active electrode/s back to the RF generator across a surface area that is much greater than the active electrode. The current is concentrated at the active electrode/s to create a therapeutic hyperthermic lesion but becomes less concentrated at the DRP when spread across its large surface area to create minimal heating. However, due to multiple factors, serious skin burns can occur around the DRP-skin interface, particularly at the side edges or corners of the DRP's conductive surface, due to the electric fields from the RF generator typically being the strongest at the edges or corners thereof. Thus, skin burns typically occur around the perimeter of the conductive area. In addition, improper placement and usage as well as sub-optimal skin surface conditions (such as excessive dryness and hair) can also contribute to skin burns. Such skin burns can result in procedural complications and patient dissatisfaction. Solutions that have attempted to address this problem have used multiple DRPs and/or monitoring techniques such as measuring the temperature of the DRP and monitoring the load balance in a split ground pad configuration. Previous solutions, however, can be costly and do not address an active mitigation approach.

Thus, the art is continuously seeking new and improved systems and methods that address the aforementioned issues. Accordingly, the present disclosure is directed to a dispersive return pad constructed of a phase change material that provides active thermal management during an ablation procedure.

SUMMARY OF THE INVENTION

Objects and advantages of the invention will be set forth in part in the following description, or may be obvious from the description, or may be learned through practice of the invention.

In one aspect, the present invention is directed to a dispersive return pad for a radiofrequency (RF) ablation procedure. The dispersive return pad includes a skin material adapted to be worn on a patient's skin, a conductive material positioned adjacent to the skin material, a non-conductive material surrounding the conductive material, and a phase-change material surrounding at least a portion of a side edge of the conductive material. Further, the phase-change material is configured to undergo a phase transition at a target temperature range corresponding to a non-damaging hyperthermic temperature range for the patient's skin. As such, the phase-change material is configured to absorb excess heating from the RF ablation procedure and to prevent burns to the patient's skin.

In one embodiment, the phase-change material completely surrounds the side edge of the conductive material. In another embodiment, the phase-change material undergoes the phase transition within an ISO IEC 60601 maximum allowable temperature rise of six (6) degrees Celsius (° C.). In further embodiments, the target temperature range for the phase transition may be less than about 43° C. For example, in one embodiment, the target temperature range for the phase transition may range from about 40° C. to about 42° C.

In additional embodiments, the phase-change material may cover an entire surface of the conductive material opposite the skin material (i.e. in addition to the side edges of the conductive material). In several embodiments, the phase-change material may also include a heat-activated color changing film or pigment incorporated therein that provides a visual indicator of the phase transition.

In particular embodiments, the skin material may also include one or more insulation layers. In such embodiments, when in contact with the patient's skin, the skin material may equilibrate to a core body temperature of about 37° C. due to the one or more insulation layers.

In another embodiment, the RF ablation procedure may have a maximum duration period of less than three (3)

minutes so as to minimize an amount of the phase-change material and mitigate any rising temperature within the duration period.

In further embodiments, the phase-change material may be paraffin wax, non-paraffin organics, hydrated salts, one or more metallic materials, or any other suitable phase-change material. In addition, in particular embodiments, the conductive material may be a metallic film at least partially covered with an electrically-conductive gel material.

In another aspect, the present disclosure is directed to a radiofrequency ablation system for performing an RF ablation procedure. The radiofrequency ablation system includes an energy source for delivering energy to a patient's body, one or more energy delivery devices electrically coupled to the energy source, and a dispersive return pad electrically coupled to the energy source. The dispersive return pad includes a skin material adapted to be worn on a patient's skin, a conductive material positioned adjacent to the skin material, a non-conductive material surrounding the conductive material, and a phase-change material surrounding at least a portion of a side edge of the conductive material. Further, the phase-change material is configured to undergo a phase transition at a target temperature range corresponding to a non-damaging hyperthermic temperature range for the patient's skin. As such, the phase-change material is configured to absorb excess heating from the RF ablation procedure and to prevent burns to the patient's skin. It should also be understood that the radiofrequency ablation system may further include any of the additional features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a portion of one embodiment of a system for applying radiofrequency electrical energy to a patient's body according to the present disclosure;

FIG. 2 illustrates a perspective cut-away view of one embodiment of a distal tip region of a probe assembly according to the present disclosure;

FIG. 3 illustrates two probes placed within an intervertebral disc to perform a radiofrequency ablation procedure according to the present disclosure;

FIG. 4 illustrates a perspective view of one embodiment of the dispersive return pad according to the present disclosure;

FIG. 5 illustrates a cross-sectional view of one embodiment of the dispersive return pad according to the present disclosure; and FIG. 6 illustrates a cross-sectional view of another embodiment of the dispersive return pad according to the present disclosure.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to the region of tissue that has been irreversibly damaged as a result of the application of thermal energy, and the invention is not intended to be limited in this regard. Furthermore, for the purposes of this description, proximal generally indicates that portion of a device or system next to or nearer to a user (when the device is in use), while the term distal generally indicates a portion further away from the user (when the device is in use).

Referring now to the drawings, FIG. 1 illustrates a schematic diagram of one embodiment of a radiofrequency (RF) ablation system 100 for performing an RF ablation procedure according to the present invention. As shown, the ablation system 100 includes an energy source 102 for delivering energy to a patient's body, a plurality of probe assemblies 106 (only one of which is shown) electrically coupled to the energy source 102 via one or more cables 104, a dispersive return pad 120 electrically coupled to the energy source 102, one or more cooling devices 108, a pump cable 110, one or more proximal cooling supply tubes 112 and one or more proximal cooling return tubes 114.

As shown in the illustrated embodiment, the energy source 102 is a radiofrequency (RF) generator, but may optionally be any power source that may deliver other forms of energy, including but not limited to microwave energy, thermal energy, ultrasound and optical energy. Further, the energy source 102 may include a display incorporated therein. The display may be operable to display various aspects of a treatment procedure, including but not limited to any parameters that are relevant an ablation procedure, such as temperature, impedance, etc. and errors or warnings related to a treatment procedure. If no display is incorporated into the energy source 102, the energy source 102 may include means of transmitting a signal to an external display. In one embodiment, the energy source 102 is operable to communicate with one more devices, for example with one or more of the probe assemblies 106 and/or the one or more cooling devices 108. Such communication may be unidirectional or bidirectional depending on the devices used and the procedure performed.

In addition, as shown, a distal region 124 of the cable 104 may include a splitter 130 that divides the cable 104 into two or more distal ends 136 such that the probe assemblies 106 can be connected thereto. A proximal end 128 of the cable 104 is connected to the energy source 102. This connection can be permanent, whereby, for example, the proximal end 128 of the cable 104 is embedded within the energy source 102, or temporary, whereby, for example, the proximal end 128 of cable 104 is connected to energy source 102 via an electrical connector. The two or more distal ends 136 of the cable 104 terminate in connectors 140 operable to couple to the probe assemblies 106 and establish an electrical connection between the probe assemblies 106 and the energy source 102. In alternate embodiments, the system 100 may include a separate cable for each probe assembly 106 being used to couple the probe assemblies 106 to the energy source 102. Alternatively, the splitter 130 may include more than two distal ends. Such a connector is useful in embodiments having more than two devices connected to the energy source 102, for example, if more than two probe assemblies are being used.

The cooling device(s) 108 may include any means of reducing a temperature of material located at and proximate to one or more of the probe assemblies 106. For example, the cooling devices 108 may include a pump assembly having one or more peristaltic pumps operable to circulate a fluid from the cooling devices 108 through one or more proximal cooling supply tubes 112, the probe assemblies 106, one or more proximal cooling return tubes 114 and back to the one or more cooling devices 108.

Still referring to FIG. 1, the proximal cooling supply tubes 112 may include proximal supply tube connectors 116 at the distal ends of the one or more proximal cooling supply tubes 112. Additionally, the proximal cooling return tubes 114 may include proximal return tube connectors 118 at the distal ends of the one or more proximal cooling return tubes 114. In one embodiment, the proximal supply tube connectors 116 are female luer-lock type connectors and the proximal return tube connectors 118 are male luer-lock type connectors although other connector types are intended to be within the scope of the present invention.

The probe assembly 106 may also include a proximal region 160, a handle 180, a hollow elongate shaft 184, and a distal tip region 190 that includes the one or more energy delivery devices 192. Further, as shown, the proximal region 160 includes a distal cooling supply tube 162, a distal supply tube connector 166, a distal cooling return tube 164, a distal return tube connector 168, a probe assembly cable 170, and a probe cable connector 172. In such embodiments, the distal cooling supply tube 162 and distal cooling return tube 164 are flexible to allow for greater maneuverability of the probe assemblies 106, but alternate embodiments with rigid tubes are possible.

The probe cable connector 172 may be located at a proximal end of the probe assembly cable 170 and may be operable to reversibly couple to one of the connectors 140, thus establishing an electrical connection between the energy source 102 and the probe assembly 106. The probe assembly cable 170 may include one or more conductors depending on the specific configuration of the probe assembly 106. For example, in one embodiment, the probe assembly cable 170 may include five conductors allowing probe assembly cable 170 to transmit RF current from the energy source 102 to the one or more energy delivery devices 192 as well as to connect multiple temperature sensing elements to the energy source 102 as discussed below.

The energy delivery devices 192 may include any means of delivering energy to a region of tissue adjacent to the distal tip region 190. For example, the energy delivery devices 192 may include an ultrasonic device, an electrode or any other energy delivery means and the invention is not limited in this regard. Similarly, energy delivered via the energy delivery devices 192 may take several forms including but not limited to thermal energy, ultrasonic energy, radiofrequency energy, microwave energy or any other form of energy. For example, in one embodiment, the energy delivery devices 192 may include an electrode. The active region of the electrode may be 2 to 20 millimeters (mm) in length and energy delivered by the electrode is electrical energy in the form of current in the RF range. The size of the active region of the electrode can be optimized for placement within an intervertebral disc; however, different sizes of active regions, all of which are within the scope of the present invention, may be used depending on the specific procedure being performed. In some embodiments, feedback from the energy source 102 may automatically adjust the exposed area of the energy delivery device 192 in response to a given measurement such as impedance or temperature.

Still referring to FIG. 1, the ablation system 100 may also include a controller 122 for facilitating communication between the energy source 102, the dispersive return pad 120, and/or the cooling devices 108. In this way, feedback control is established between the cooling devices 108 and the energy source 102. The feedback control may include the energy source 102, the probe assemblies 106, the dispersive return pad 120, and/or the cooling devices 108, although any feedback between any two devices is within the scope of the present invention. The feedback control may be implemented, for example, in a control module which may be a component of the energy source 102. In such embodiments, the energy source 102 is operable to communicate bi-directionally with the probe assemblies 106 as well as with the dispersive return pad 120 and/or the cooling devices 108. In the context of this invention, bi-directional communication refers to the capability of a device to both receive a signal from and send a signal to another device.

Referring now to FIG. 2, the energy delivery devices 192 may also include a temperature sensing element 132 that protrudes beyond a distal end thereof. More specifically, as shown, the temperature sensing element 132 may have a length 414 of less than about 1 millimeter (mm) that extends from a distal end 194 of the energy delivery device 192. Accordingly, the temperature sensing elements 132 are configured to control and optimize the size of the lesion for different anatomical locations, for instance creating smaller lesions in regions adjacent to critical structures such as arteries and motor nerves.

In addition, the temperature sensing element 132 is configured to increase (or decrease) a power demand of the energy delivery device 192. Further, as shown, the temperature sensing element 132 may include a stainless steel hypotube 134 that is electrically conductive and may be electrically coupled to the energy delivery device 192. Thus, in such an embodiment, whereby energy may be conducted to the protrusion and delivered from the protrusion to surrounding tissue, the protrusion may be understood to be a component of both temperature sensing element 132 as well as the one or more energy delivery devices 192. Placing the temperature sensing elements 132 at this location, rather than within a lumen 138 defined by the energy delivery device 192, is beneficial because it allows the temperature sensing element 132 to provide a more accurate indication of the temperature of tissue proximate to the energy delivery device 192. This is due to the fact that, when extended beyond the energy delivery device 192, the temperature sensing element 132 will not be as affected by the cooling fluid flowing within the lumen 138 as it would be were it located within lumen 138. Thus, in such embodiments, the probe assembly 106 includes a protrusion protruding from the distal region of the probe assembly, whereby the protrusion is a component of the temperature sensing element 132.

Referring now to FIG. 3, in one embodiment, the first and second probe assemblies 106 may be operated in a bipolar mode. For example, as shown, FIG. 3 illustrates one embodiment of two probe assemblies 106, wherein the distal tip regions 190 thereof are located within an intervertebral disc 142. In such embodiments, electrical energy is delivered to the first and second probe assemblies 106 and this energy is preferentially concentrated therebetween through a region of tissue to be treated (i.e. an area of the intervertebral disc 142). The region of tissue to be treated is thus heated by the energy concentrated between first and second probe assemblies 106. In other embodiments, the first and second probe assemblies 106 may be operated in a monopolar mode, in which case an additional grounding pad is required on the surface of a body of a patient, as is known in the art. Any combination of bipolar and monopolar procedures may also be used. It should also be understood that the system may include more than two probe assemblies. For example, in some embodiments, three probe assemblies may be used and the probe assemblies may be operated in a triphasic mode, whereby the phase of the current being supplied differs for each probe assembly.

Referring now to FIGS. 4 and 5, various views of the dispersive return pad 120 according to the present disclosure are illustrated. FIG. 4 illustrates a perspective view of one embodiment of the dispersive return pad 120 according to the present disclosure. FIG. 5 illustrates a cross-sectional view of one embodiment of the dispersive return pad 120 according to the present disclosure is illustrated. As shown in FIG. 4, the dispersive return pad 120 may be electrically coupled to the energy source 102, e.g. via one or more cables 126. As shown in FIG. 5, the dispersive return pad 120 may be constructed of multiple layers. More specifically, as shown, the dispersive return pad 120 may include a skin material 144 adapted to be worn on a patient's skin. In addition, as shown, the dispersive return pad 120 may include a conductive material 146 positioned adjacent to the skin material 144. For example, in particular embodiments, the conductive material 146 may be a metallic film at least partially covered with an electrically-conductive gel material. Further, the dispersive return pad 120 may include a non-conductive material 148 surrounding and/or the conductive material 146. For example, in one embodiment, the non-conductive material 148 may be a plastic or polymer-based material.

Still referring to FIGS. 4 and 5, the dispersive return pad 120 may further include a phase-change material 150 surrounding at least a portion of one or more of the side edges 152 of the conductive material 146. In one embodiment, as shown particularly in FIG. 4, the phase-change material 150 may completely surround the side edges 152 of the conductive material 146. It should be understood that the any amount of phase-change material 150 may be incorporated into the dispersive return pad 120 in any suitable arrangement. By at least partially surrounding the side edges 152 of the conductive material 146, the phase-change material 150 is configured to reduce the occurrence of skin burns to the patient as the electric fields are typically strongest at the edges/corners of the conductive material 146. As such, the placement of the phase-change material 150 can be limited to the side edges 152 of the conductive pad 146 to minimize the amount of material needed.

Accordingly, the phase-change material 150 is configured to undergo a phase transition at a target temperature range corresponding to a non-damaging hyperthermic temperature range for the patient's skin. As such, the phase-change material 150 is configured to absorb excess heating from the RF ablation procedure and to prevent burns to the patient's skin. In another embodiment, the phase-change material 150 may undergo the phase transition within an ISO IEC 60601 maximum allowable temperature rise, e.g. about 6° C. In further embodiments, the target temperature range for the phase transition may be less than about 43° C. For example, in one embodiment, the target temperature range for the phase transition may range from about 40° C. to about 42° C.

In additional embodiments, as shown in FIG. 6, the phase-change material 50 may cover an entire surface, e.g. the top surface 154, of the conductive material 146 opposite the skin material 144 (i.e. in addition to the side edges 152 of the conductive material 146). More specifically, in certain embodiments, the phase-change material 150 may be paraffin wax, non-paraffin organics, hydrated salts, one or more metallic materials, or any other suitable phase-change material. In several embodiments, the phase-change material 150 may also include a heat-activated color changing film or pigment incorporated therein that provides a visual indicator of the phase transition.

Referring to FIGS. 5 and 6, the skin material 144 may also include one or more insulation layers 156. In such embodiments, when in contact with the patient's skin, the skin material 144 may equilibrate to a core body temperature of the patient, e.g. of about 37° C., due to the insulation layer(s) 156. In another embodiment, the ablation procedure(s) described herein may have a maximum duration period of less than three (3) minutes, i.e. so as to minimize the amount of the phase-change material 150 in the dispersive return pad 120 and/or to mitigate any rising temperature within the duration period.

An ablation system having a dispersive return pad according to the present invention may be used in various medical procedures where the potential for burns to a patient's skin is present. Specifically, the ablation system of the present invention is particularly useful for procedures involving treatment of back pain, including but not limited to treatments of tumors, intervertebral discs, facet joint denervation, sacroiliac joint lesioning or intraosseous (within the bone) treatment procedures. Moreover, the ablation system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A dispersive return pad for a radiofrequency (RF) ablation procedure, the dispersive return pad comprising:
    a skin material adapted to be adhered on a patient's skin;
    a conductive material having a top face, a bottom face, and four side edges that are perpendicular to the top face and the bottom face, the bottom face of the conductive material positioned adjacent to the skin material;
    a phase-change material surrounding the four side edges of the conductive material, the phase-change material positioned: i) adjacent to and in contact with only the four side edges of the conductive material and ii) on top of the skin material, the phase-change material being configured to undergo a phase transition at a target temperature range corresponding to a non-damaging hyperthermic temperature range for the patient's skin, the phase-change material configured to absorb excess heating from the RF ablation procedure and to prevent burns to the patient's skin; and
    a non-conductive material that is different from the skin material, the conductive material, and the phase-change material, the non-conductive material encapsulating the conductive material and the phase-change material.

2. The dispersive return pad of claim 1, wherein the phase-change material undergoes the phase transition within an ISO IEC 60601 maximum allowable temperature rise of six (6) degrees Celsius (° C.).

3. The dispersive return pad of claim 1, wherein the target temperature range of the phase transition is less than about 43 degrees Celsius (° C.).

4. The dispersive return pad of claim 3, wherein the target temperature range of the phase transition ranges from about 40 degrees Celsius (° C.) to about 42° C.

5. The dispersive return pad of claim 1, wherein the phase-change material further comprises a heat-activated color changing film or pigment incorporated therein that provides a visual indicator of the phase transition.

6. The dispersive return pad of claim 1, wherein the skin material further comprises one or more insulation layers, and wherein, when in contact with the patient's skin, the skin material equilibrates to a core body temperature of about 37° C. due to the one or more insulation layers.

7. The dispersive return pad of claim 1, wherein the RF ablation procedure has a maximum duration period of less than three (3) minutes so as to minimize an amount of the phase-change material and mitigate any rising temperature within the duration period.

8. The dispersive return pad of claim 1, wherein the phase-change material comprises at least one of paraffin wax, non-paraffin organics, hydrated salts, or one or more metallic materials.

9. The dispersive return pad of claim 1, wherein the conductive material comprises a metallic film at least partially covered with an electrically-conductive gel material.

10. A radiofrequency ablation system for performing a radiofrequency (RF) ablation procedure, comprising:
    an energy source for delivering energy to a patient's body;
    one or more energy delivery devices electrically coupled to the energy source; and,
    a dispersive return pad electrically coupled to the energy source, the dispersive return pad comprising:
        a skin material adapted to be worn on a patient's skin;
        a conductive material having a top face, a bottom face, and four side edges that are perpendicular to the top face and the bottom face, the bottom face positioned adjacent to the skin material;
        a phase-change material surrounding the four side edges of the conductive material, the phase-change material positioned: i) adjacent to and in contact with only the four side edges of the conductive material and ii) on top of the skin material, the phase-change material being configured to undergo a phase transition at a target temperature range corresponding to a non-damaging hyperthermic temperature range for the patient's skin, the phase-change material configured to absorb excess heating from the RF ablation procedure and to prevent burns to the patient's skin; and
        a non-conductive material that is different from the skin material, the conductive material, and the phase-change material, the non-conductive material encapsulating the conductive material and the phase-change material.

11. The radiofrequency ablation system of claim 10, wherein the phase-change material undergoes the phase transition within an ISO IEC 60601 maximum allowable temperature rise of six (6) degrees Celsius (° C.).

12. The radiofrequency ablation system of claim 10, wherein the target temperature range is less than about 43 degrees Celsius (° C.).

13. The radiofrequency ablation system of claim 10, wherein the phase-change material further comprises a heat-activated color changing film or pigment incorporated therein that provides a visual indicator of the phase transition.

14. The radiofrequency ablation system of claim 10, wherein the skin material of the dispersive return pad further comprises one or more insulation layers, and wherein, when in contact with the patient's skin, the skin material equilibrates to a core body temperature of about 37° C. due to the one or more insulation layers.

15. The radiofrequency ablation system of claim 10, wherein the RF ablation procedure has a maximum duration period of less than three (3) minutes so as to minimize an amount of the phase-change material and mitigate any rising temperature within the duration period.

16. The radiofrequency ablation system of claim 10, wherein the phase-change material of the dispersive return pad is at least one of paraffin wax, non-paraffin organics, hydrated salts, or one or more metallic materials, and wherein the conductive material is a metallic film at least partially covered with an electrically-conductive gel material.

* * * * *